United States Patent [19]
Popken

[11] Patent Number: 5,725,530
[45] Date of Patent: Mar. 10, 1998

[54] SURGICAL SAW AND METHODS THEREFOR

[76] Inventor: John A. Popken, 3909 Bogey Ct., Longmont, Colo. 80503

[21] Appl. No.: 665,832

[22] Filed: Jun. 19, 1996

[51] Int. Cl.⁶ ..................................................... A61B 17/14
[52] U.S. Cl. .......................... 606/82; 606/79; 606/176; 606/183; 30/166.3; 30/381
[58] Field of Search ............................. 606/79, 82, 171, 606/176–178, 180, 183; 30/166.3, 381

[56] References Cited

U.S. PATENT DOCUMENTS

| | | |
|---|---|---|
| 1,201,467 | 10/1916 | Hoglund . |
| 1,543,195 | 7/1925 | Thygesen et al. . |
| 3,495,590 | 2/1970 | Zeiller . |
| 4,019,408 | 4/1977 | Idel . |
| 4,184,804 | 1/1980 | Stohlmann . |
| 4,273,169 | 6/1981 | Baenen . |
| 4,461,296 | 7/1984 | Hodge . |
| 4,584,999 | 4/1986 | Arnegger . |
| 4,637,391 | 1/1987 | Schlein . |
| 4,683,924 | 8/1987 | Cornelius . |
| 4,700,702 | 10/1987 | Nilsson . |
| 4,892,093 | 1/1990 | Zarnowski et al. . |
| 5,092,869 | 3/1992 | Waldron . |
| 5,100,506 | 3/1992 | Sturtevant et al. . |
| 5,133,728 | 7/1992 | Petersen . |
| 5,135,533 | 8/1992 | Petersen et al. . |
| 5,178,626 | 1/1993 | Pappas . |
| 5,306,285 | 4/1994 | Miller et al. . |
| 5,439,472 | 8/1995 | Evans et al. . |
| 5,496,325 | 3/1996 | McLees . |

FOREIGN PATENT DOCUMENTS

| | | | |
|---|---|---|---|
| 2615301 | 10/1977 | Germany . | |
| 2640267 | 5/1978 | Germany . | |
| 2935732 | 3/1981 | Germany . | |
| 322599 | 11/1934 | Italy ................. | 30/166.3 |
| 454753 | 2/1950 | Italy . | |

*Primary Examiner*—Michael Buiz
*Assistant Examiner*—Daphna Shai

[57] ABSTRACT

A surgical saw includes a saw assembly for being driven by a powered surgical handpiece and having a pair of parallel, co-planar guide arms, a pair of flexible, endless cutting bands disposed around the guide arms, respectively, and a drive mechanism for driving the cutting bands around the guide arms in a cutting direction. The cutting bands each include a plurality of spaced cutting teeth connected to one another by flexible band segments. The cutting bands are driven by the drive mechanism relative to the guide arms in opposite directions along defined paths to cut anatomical tissue at distal ends of the guide arms. A method of resecting bone includes the steps of driving the cutting bands relative to the guide arms in the cutting direction along the defined paths and inserting the distal ends of the guide arms in the bone to resect the bone along the plane of the guide arms.

25 Claims, 4 Drawing Sheets

SURGICAL SAW AND METHODS THEREFOR

BACKGROUND OF THE INVENTION

1. Field of the Invention

The present invention relates generally to surgical saws and, more particularly, to surgical bone saws having flexible, endless cutting blades and to methods therefor.

2. Description of the Prior Art

Surgical saws are utilized in the course of many various procedures to resect or cut anatomical tissue including bone. For example, during the performance of total knee replacement surgery, several bone cuts are made in the knee to prepare, contour or shape the knee to receive a prosthesis. Five cuts are generally made in the distal femur, i.e. transverse distal femoral cut, anterior femoral cut, posterior femoral cut and anterior and posterior chamfer cuts. One cut is usually made in the proximal tibia, i.e. transverse proximal tibial cut, and another cut is usually made in the patella to remove the patellar facets. Such bone cuts are typically made with an end cutting oscillating saw having a flat saw blade driven to sweep back and forth, up to thousands of times per minute, while being advanced into the bone. In order to accurately resect the bone to fit the contours of the prosthesis, cutting blocks are usually attached to the bone and used to guide the saw blade to establish the proper orientation for the bone cuts. Conventional cutting blocks commonly have slots through which the saw blade is inserted, the slots having sufficient clearance to allow the saw blade to oscillate while maintaining a close enough fit with the saw blade to guide the saw blade to obtain the proper bone cut. Illustrative of end cutting oscillating saw blades for resecting bone are U.S. Pat. No. 4,513,742 and U.S. Pat. No. 4,584,999 to Arnegger U.S. Pat. No. 5,087,261 to Ryd et al, U.S. Pat. No. 5,263,972 and U.S. Pat. No. 5,439,472 to Evans et al, which also disclose power drive systems for driving the saw blades, and U.S. Pat. No. 5,306,285 to Miller et al. Representative of cutting guides or blocks for guiding end cutting oscillating saw blades to form bone cuts are U.S. Pat. No. 4,892,093 to Zarnowski, U.S. Pat. No. 5,092,869 to Waldron and U.S. Pat. No. 5,178,626 to Pappas.

Conventional end cutting oscillating bone saws and guide systems therefor have many disadvantages including excessive vibration of the bone saws resulting in inaccurate bone cuts and poor surface finishes, elevated temperatures of the bone saws due to friction between the saw blades and the cutting blocks and/or between the saw blades and the bone, thermal-necrosis of the bone due to the high temperatures caused by friction, the inability to use cementless prostheses where healthy bone is damaged from high temperatures, production of metal debris from contact of the saw blades with the cutting blocks, consumption of an exorbitant amount of power by the drive systems for the bone saws, the need for larger, more expensive batteries due to the high power requirements of the drive systems, excessive noise generated by the drive systems, increased risk of contamination to medical personnel from blood-borne and other pathogens carried by anatomical tissue and fluids that are splattered, atomized or comminuted by the oscillating saw blades, limitations on the depth of bone cuts able to be obtained due to the increased mass presented by the relatively long, oscillating saw blades, a reduction in safety for medical personnel due to the increased cutting field arising from the relatively greater length of the saw blades, over-stressing of the drive systems due to the relatively greater mass and length of the moving saw blades and difficulties in guiding the oscillating saw blades.

SUMMARY OF THE INVENTION

Accordingly, it is a primary object of the present invention to overcome the aforementioned disadvantages of prior art surgical saws and methods of resecting bone.

Another object of the present invention is to resect anatomical tissue utilizing a surgical saw comprising a pair of flexible, endless cutting bands driven in defined paths around parallel, stationary guide arms.

A further object of the present invention is to provide a flexible, endless cutting band having cutting teeth and band segments of integral, unitary construction for being driven relative to a stationary guide arm in a cutting direction to cut anatomical tissue.

It is also an object of the present invention to provide a guard to prevent cutting along most of the outer sides of a pair of co-planar guide arms around which a pair of cutting bands are driven, respectively.

Yet another object of the present invention is to provide a flexible, endless cutting band of a surgical saw having spaced cutting teeth connected by band segments with the cutting edges of alternate cutting teeth protruding laterally beyond the band segments in opposite directions.

An additional object of the present invention is to maintain parallelism of the stationary guide arms of a surgical saw having endless, flexible cutting bands driven around the guide arms.

The present invention has as a further object to resect bone by inserting distal ends of co-planar, parallel guide arms into the bone and driving cutting bands relative to and around the guide arms in a cutting direction to resect the bone along the plane of the guide arms.

Some of the advantages of the present invention are that friction between the guide arms and a guide block attached to the bone is minimized, friction between the guide arms and the bone is also minimized, operating temperatures of the surgical saw are relatively lower than conventional end cutting oscillating saws, thermal-necrosis of the bone is avoided allowing the use of cementless prostheses or implants, the surgical saw has a significantly greater number of cutting teeth than conventional end cutting saws for enhanced, more efficient cutting with less tooth wear, the surgical saw can be operated at lower speeds for reduced power requirements as well as friction, cutting debris is removed from the operative or cutting site via a passage between the guide arms in continuous flow cutting, splattering of tissue and/or fluids is reduced with a concomitant reduction in the risk of contamination to operating personnel, the surgical saw is self-centering and nullifies side thrusts, the guide arms are of reduced mass for greater stability, bone cuts can be obtained to greater depths, the surgical saw can be more precisely guided during cutting, undesired cutting of soft tissue is avoided, parallelism of the guide arms is maintained with the use of a cutting guide for an accurate cut, the surgical saw can be utilized with conventional powered handpieces, and the surgical saw can be utilized with conventional guide blocks affixed to the bone.

These and other objects, benefits and advantages are realized with the present invention as characterized in a surgical saw comprising a saw assembly for being driven by a powered surgical handpiece. The saw assembly includes a pair of guide arms, a pair of flexible, endless cutting bands disposed around the guide arms, respectively, a drive mechanism for driving the cutting bands in defined paths and a housing mounting the guide arms and the drive mechanism. The guide arms have proximal ends disposed in the housing and distal ends protruding beyond the housing, with the guide arms being mounted in parallel, co-planar relationship. The cutting bands each include a plurality of spaced cutting teeth connected by flexible band segments. According to a preferred embodiment, the cutting bands are each formed unitarily, integrally as a single piece. The drive mechanism is disposed in the housing and includes a pair of sprocket wheels for being driven by the handpiece. Each sprocket wheel is disposed at a proximal end of a guide arm, and each cutting band is disposed around a guide arm and its associated sprocket wheel for movement relative to the guide arm in the defined path. The sprocket wheels are rotatably drivable in opposite directions to counter-rotate the cutting bands around the guide arms and the sprocket wheels in a cutting direction to cut anatomical tissue. The guide arms are laterally spaced from one another to define a passage between the guide arms through which cutting debris is removed. A pair of guard members protrude from the housing along outer sides of the guide arms and have distal ends disposed proximally of the distal ends of the guide arms such that cutting occurs at the distal ends and is prevented along most of the outer sides of the guide arms. A cutting guide for the surgical saw includes a body having a slot therein allowing the guide arms with the cutting bands therearound and the guards to be inserted through the slot to protrude therefrom. The cutting guide stabilizes the surgical saw and maintains parallelism of the guide arms during use. A method of resecting bone according to the present invention includes the steps of driving the cutting bands in the defined paths in opposite directions relative to the guide arms and inserting the distal ends of the guide arms in the bone to resect the bone along the plane of the guide arms.

Other objects and advantages of the present invention will become apparent from the following description of the preferred embodiments taken in conjunction with the accompanying drawings wherein like parts in each of the several figures are identified by the same reference characters.

DESCRIPTION OF THE PREFERRED EMBODIMENT

Figure 1:
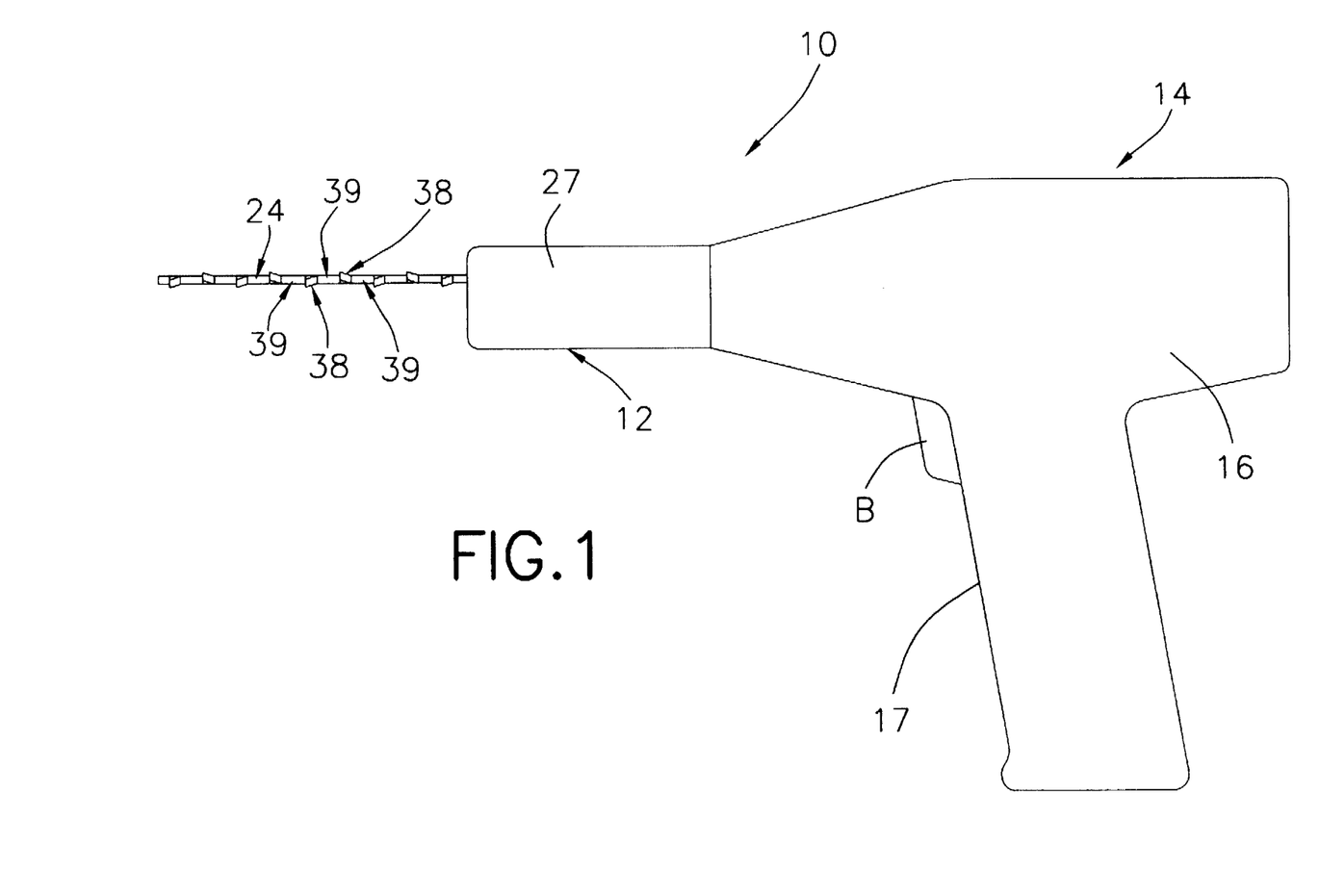
FIG. 1 is a side view of a surgical saw according to the present invention.
Figure 2:
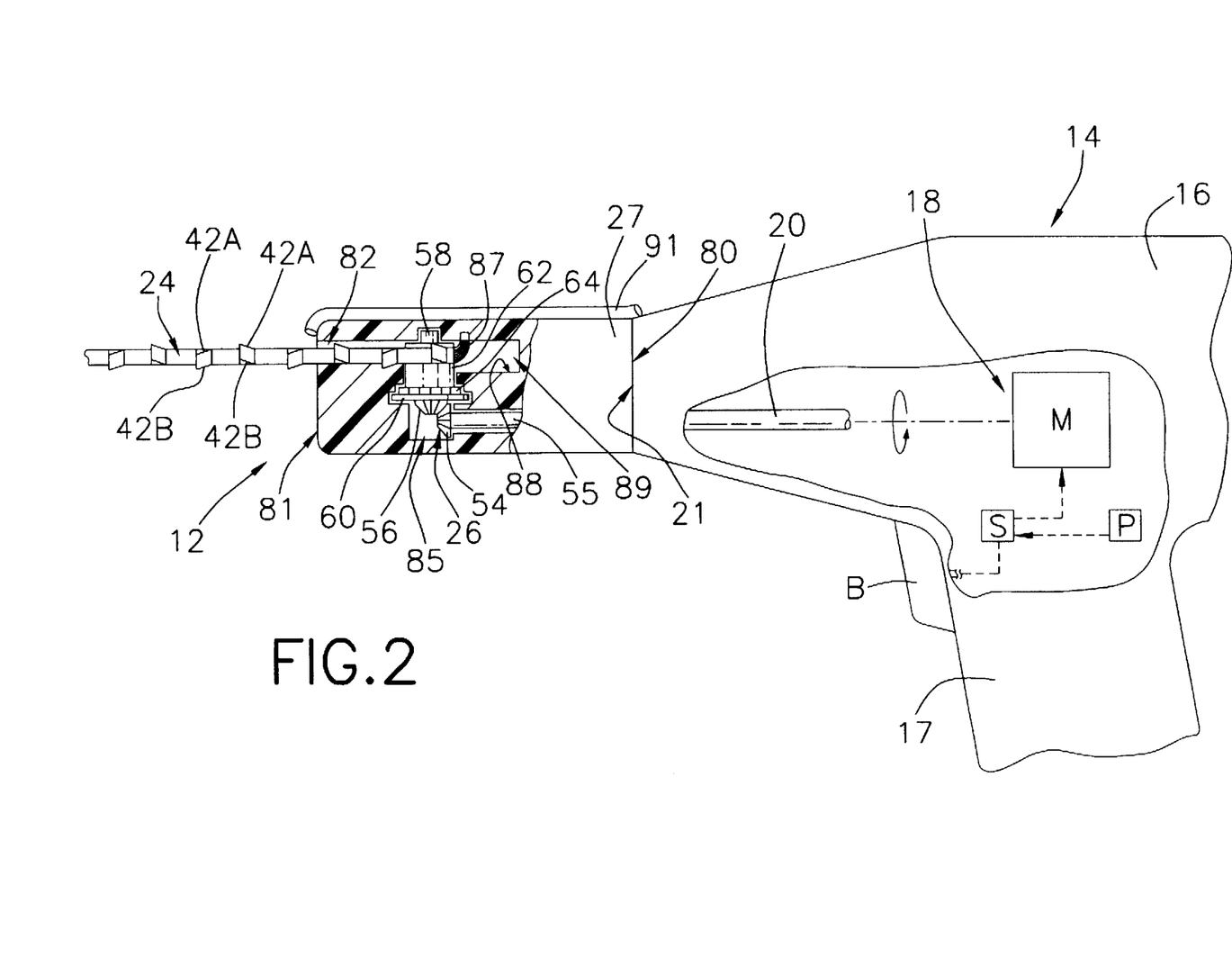
FIG. 2 is a side view, partly in section, of the surgical saw.

A surgical saw 10 according to the present invention is illustrated in FIGS. 1 and 2 and includes a saw assembly 12 and a powered surgical handpiece 14 for driving saw assembly 12. Handpiece 14 comprises a body 16 configured or provided with a handgrip 17 and a drive system 18 disposed in body 16. Drive system 18, which is illustrated schematically in FIG. 2, includes a drive motor M, a power supply P for supplying power to drive motor M, a switch S for controlling the supply of power to motor M and a pushbutton or trigger B, operable from externally of body 16, for actuating switch S. Power supply P for handpiece 14 can be an electric power supply as well as various other power supplies or sources, such as hydraulic and pneumatic, suitable to power motor M. A drive shaft 20 is mounted in body 16 to be rotatably driven by motor M. Body 16 has a forward end 21 with an opening therein aligned with drive shaft 20 allowing the drive shaft 20 to be coupled with the saw assembly 12 as explained further below. Handpiece 14 can include various conventional powered surgical handpieces such as those disclosed in U.S. Pat. No. 5,263,922 and U.S. Pat. No. 5,439,472 to Evans et al and the Sodem Power System handpieces of Sodem Systems, Geneva, Switzerland. The handpiece 14 can include various mechanisms for locking or retaining the saw assembly 12 to the handpiece 14 such as the snap lock connections of the Sodem Power System handpieces.

Figures 3, 4, 5, 6, 7, 8:
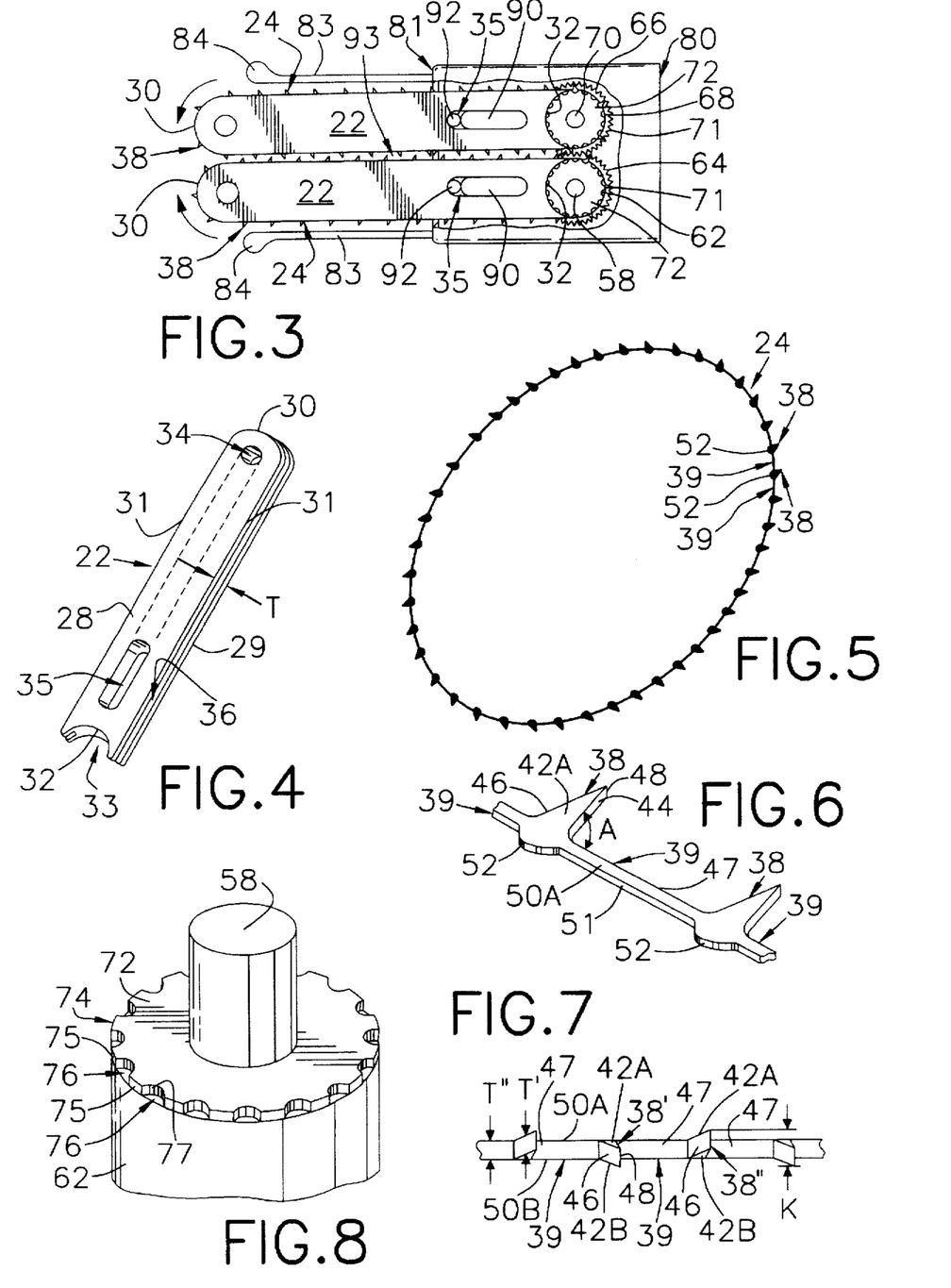
FIG. 3 is a top view of the saw assembly for the surgical saw.
FIG. 4 is a perspective view of a guide arm for the saw assembly.
FIG. 5 is a perspective view of a cutting band for the saw assembly.
FIG. 6 is an enlarged, broken perspective view of the cutting band.
FIG. 7 is a broken plan view of the cutting band.
FIG. 8 is a broken perspective view showing a sprocket wheel mounted to a drum of the saw assembly.

Saw assembly 12, as best shown in FIGS. 2 and 3, includes a pair of stationary guide arms 22, a pair of flexible, endless cutting blades or bands 24 guided by guide arms 22 for movement in prescribed or defined paths, a drive mechanism 26 for driving cutting bands 24 to move in the prescribed paths and a housing 27 mounting drive mechanism 26 and guide arms 22. Guide arms 22, as illustrated in FIG. 4, each include a flat or planar, elongate body of uniform thickness T and made of high strength, medically acceptable material. Each guide arm 22 has opposed, planar, parallel outer surfaces 28 and 29 with the thickness T between the outer surfaces 28 and 29. Each guide arm 22 is defined by an arcuate forward edge 30, straight, parallel side edges 31 merging with forward edge 30 and an arcuate rearward edge 32 joining side edges 31. Forward edges 30 and rearward edges 32 both curve in the same direction, and each forward edge is longitudinally aligned with a rearward edge. Forward edges 30 define rounded noses or tips at distal ends of the guide arms, and rearward edges 32 define partial circular recesses 33 at proximal ends of the guide arms. A hole 34 is formed through each guide arm at the distal end thereof, and an oblong or elongate slot 35 is formed through each guide arm at a proximal end thereof to be received in housing 27. Slots 35 can extend distally to merge with holes 34 as shown in dotted lines in FIG. 4 to further reduce the mass of the guide arms. A groove 36 is formed between the outer surfaces 28 and 29, i.e. along thickness T, to extend along the forward edges 30 and the side edges 31 of each guide arm.

Cutting bands 24, as best illustrated in FIG. 5, each include a plurality of spaced cutting teeth 38 connected to one another by flexible band segments 39 to form an endless, flexible band or ring. According to a preferred embodiment, cutting bands 24 are each of integral, unitary construction with teeth 38 and band segments 39, made integrally, unitarily to form a one piece, monolithic, homogeneous, flexible band of high strength, medically acceptable material. The cutting bands can be manufactured unitarily, integrally as one piece in many various ways including electric discharge machining from a single sheet of material, electric discharge machining in a continuous line that is cut and welded at opposite ends to form the endless band or ring, and punch manufacturing using forming dies and coining dies to fabricate the cutting bands. The cutting bands can each be made as a strip or length of material joined at its ends to form a band or loop. The cutting bands can also be of multi-part construction with the teeth 38 and band segments 39 made as separate pieces assembled to form the flexible, endless band or ring. For example, the band segments can be designed as links to mechanically interlock with the cutting teeth. The cutting bands can be manufactured as separate pieces in many various ways including metal injection molding, powdered metallurgy; extrusion, investment casting and forging.

As shown in FIGS. 6 and 7, each tooth 38 is defined by lateral surfaces 42A and 42B, a leading edge or surface 44 transverse or perpendicular to lateral surfaces 42A and 42B, a trailing edge or surface 46 transverse or perpendicular to lateral surfaces 42A and 42B and a thickness T' between lateral surfaces 42A and 42B. The leading surface 44 merges with an outer peripheral surface 47 of an adjacent forward band segment 39, and the trailing surface 46 merges with an outer peripheral surface 47 of an adjacent rearward band segment 39 such that a base of each tooth is disposed between two band segments. Accordingly, as shown in FIG. 7, the forward band segment 39 of cutting tooth 38' defines the rearward band segment for the next forward cutting tooth 38", and the rearward band segment 39 of tooth 38' defines the forward band segment for the next rearward cutting tooth. The leading surface 44 and the trailing surface 46 for each cutting tooth 38 meet one another at an apex defining a cutting edge 48 transverse or perpendicular to lateral surfaces 42A and 42B. Teeth 38 are angled in a forward or cutting direction from the band segments 39 with the leading surfaces 44 defining an acute rake angle A with the outer peripheral surfaces 47 of the forward band segments 39 as shown in FIG. 6. Each band segment 39 has lateral surfaces 50A and 50B merging with lateral surfaces 42A and 42B, respectively, outer peripheral surface 47 transverse or perpendicular to lateral surfaces 50A and 50B, an inner peripheral surface 51 transverse or perpendicular to lateral surfaces 50A and 50B and a thickness T" between the lateral surfaces 50A and 50B that is the same or substantially the same as the thickness T of guide arms 22. The band segments 39 space the cutting teeth 38 from one another; and, in a preferred embodiment, cutting bands 24 each include ninety cutting teeth. The cutting teeth protrude outwardly from the circumference defined by outer peripheral surfaces 47; however, depending on procedural use, the cutting teeth can protrude inwardly from the inner peripheral surfaces 51. The lateral surfaces 42A and 42B for each cutting tooth 38 are parallel to one another, and the lateral surfaces 50A and 50B for each band segment 39 are parallel to one another; however, the lateral surfaces can be non-parallel.

The cutting teeth 38 are angularly offset from the band segments 39 in a lateral direction with alternate cutting teeth 38 being angularly offset in opposite directions. As shown in FIG. 7 for alternate cutting teeth 38' and 38", the lateral surfaces 42A and 42B of cutting tooth 38' are both angled laterally from the lateral surfaces 50A and 50B of band segments 39, and the lateral surfaces 42A and 42B of cutting tooth 38" are both angled laterally in the opposite direction from the lateral surfaces 50A and 50B of band segments 39. Accordingly, the cutting edge 48 of cutting tooth 38' protrudes laterally beyond lateral surface 50B, and the cutting edge 48 of cutting tooth 38" protrudes laterally beyond the opposite lateral surface 50A such that the cutting edges of alternate teeth extend or protrude laterally beyond opposite lateral surfaces 50A and 50B. The cutting teeth 38 define a kerf K equal to the maximum lateral dimension between the lateral surfaces 42A and 42B of adjacent teeth 38. As shown in FIGS. 5 and 6, cutting teeth 38 each have a keel 52 in the form of a convex or rounded protrusion at the base of each cutting tooth 38. Each keel 52 is disposed between two band segments 39 and has an arcuate surface or edge curving outwardly from and merging with the inner peripheral surfaces 51 of the band segments, and the keels 52 can have a hook-like shape.

According to a preferred embodiment, the cutting bands are made of 17-4PH Stainless Steel. However, the cutting bands can be made of any surgical grade stainless steel having a hardness sufficient to cut bone but being sufficiently flexible to permit forming a monolithic endless band. The guide arms are preferably made of 17-4PH Stainless Steel heat treated for a hardness greater than the hardness of the cutting bands to reduce wear between the guide arms and the cutting bands. A preferred size or circumference for the cutting bands is 9 to 12 inches. A preferred thickness T for the guide arms is 0.050 inch, and a preferred thickness T" for the band segments is 0.055 inch. The cutting teeth preferably have a thickness T' less than the kerf K and equal to or greater than T". The thickness of the guide arms can be greater than T" with the groove having a width corresponding the T". The rake angle can be a standard bone cutter rake angle. The kerf K is as small as possible; and, according to a preferred embodiment, the kerf K is 0.060 inch.

Drive mechanism 26 is best shown in FIGS. 2 and 3 and includes a right angle bevel gear unit having a first bevel gear 54 rigidly carried by an input shaft 55 and a second bevel gear 56 rigidly carried by an output shaft 58. The input shaft 55 is adapted to be mechanically coupled with the drive shaft 20 of handpiece 14. The input shaft 55 can be coupled with the handpiece drive shaft 20 in many various ways including various conventional mechanisms such as slotted shafts, snap lock connections, and locking rings conventionally used to couple surgical powered handpieces with adapters or attachments therefor. The second bevel gear 56 is arranged to be rotatably driven by the first bevel gear 54; and, accordingly, the output shaft 58 of the bevel gear unit is offset 90° from the drive shaft 20 of handpiece 14. The bevel gears 54 and 56 have a 1 to 1 ratio to rotate at the same speed as the handpiece drive shaft 20. A bearing plate 60 is fixedly attached to the output shaft 58 to rotate therewith, the plate 60 having a central aperture through which the output shaft 58 passes. Plate 60 is interposed between bevel gear 56 and a cylindrical drum or sleeve 62 rigidly disposed over output shaft 58 to be rotated thereby, the output shaft 58 passing through an axial bore of drum 62. Drum 62 carries or is formed with a gear 64 at a lower end thereof, and a gear 66 rigidly carried by or formed at a lower end of a second cylindrical drum or sleeve 68 is arranged in rotatably driven engagement with gear 64. A shaft 70 passes through an axial bore or lumen of drum 68 and is rigidly affixed thereto for rotation therewith. Gears 64 and 66, which can be formed integrally, unitarily with drums 62 and 68, respectively, or separately therefrom, each have a plurality of spaced teeth 71 adapted for driving engagement such that gears 64 and 66 are rotatably driven in opposite directions when gear 64 is rotated by the bevel gear unit. The counter rotating gears 64 and 66 have a 1 to 1 ratio such that drums 62 and 68 counter-rotate at the same speed. Sprocket or cog wheels 72 are rigidly attached to upper ends of drums 62 and 68, respectively, for rotation therewith, the sprocket wheels 72 having central apertures through which shafts 58 and 70 pass, respectively. One sprocket wheel 72 is shown in FIG. 8 mounted to drum 62 and includes a circular plate of uniform minimal thickness and having sprockets or cogs 74 along the circumference thereof defined by segments 75 of the circumferential edge or surface of wheel 72 and partial circular spaces 76 between segments 75. Each space 76 is defined by an arcuate edge or surface 77 extending between segments 75 and has a size and configuration to receive keels 52 of cutting teeth 38.

Housing 27 can have any desirable external configuration including a substantially rectangular external configuration as shown in FIG. 2. Housing 27 has a rearward end 80 with an opening or passage therein aligned with shaft 55 allowing shaft 55 to be coupled with the handpiece drive shaft 20. The housing 27 has a forward end 81 with a channel 82 therein through which the guide arms 22 protrude when the proximal ends of the guide arms are coupled with the drive mechanism as explained further below. As shown in FIG. 3, a guard including a pair of elongate guard members 83 protrude from forward end 81 to extend in the distal direction. Each guard member 83 extends from housing 27 to an outwardly flared distal end having a rounded or blunt distal tip 84. Guard members 83 are permanently or releasably attached or coupled to housing 27 such that the guide arms 22 are disposed between the guard members 83 in lateral alignment therewith as shown in FIG. 3. The guard members 83 have a length such that the distal tips 84 are disposed proximally of the forward edges 30 of guide arms 22 allowing a distal end of the saw assembly to be utilized to cut anatomical tissue while preventing cutting along most of the outer sides of the guide arms 22 as explained further below. The guard members are preferably made of tempered stainless steel; and, according to a preferred embodiment, the distal ends of the guide arms protrude beyond the tips of the guard members ¼ inch. The thickness of the guard members is the same as or smaller than the kerf K of the cutting teeth allowing the guard members to follow the distal ends of the guide arms into anatomical tissue during cutting.

Housing 27 has an internal recess 85, shown in FIG. 2, for accommodating drive mechanism 26 with an internal shoulder of the housing supporting plate 60 and gears 64 and 66. The drive mechanism 26 is arranged in housing 27 as shown in FIG. 2 with shaft 55 rotatably mounted in a passage in the rearward end 80 of housing 27 and with shafts 58 and 70 rotatably mounted in recesses in an upper wall of the housing. If desired, a brush can be disposed in the housing to remove debris from the cutting teeth when the cutting bands are driven by the drive mechanism as explained further below. As shown in FIG. 2, a brush 87 is attached to an internal surface of the housing upper wall to remove debris from the cutting teeth 38. A ledge 88 within recess 85 defines a sump 89 in housing 27 for collecting debris removed from teeth 38 by brush 87. The sump 89 is separated from the gears by the ledge 88 and; if desired, a seal can be disposed around the drums 62 and 68 adjacent ledge 92. The housing can be designed with an access door or panel communicating with sump 89 allowing debris to be removed therefrom. A pair of oblong lands 90, shown in FIG. 3, protrude upwardly from ledge 88 at the forward end of the housing. Lands 90 are longitudinally aligned with shafts 58 and 70, respectively, and have lateral and longitudinal dimensions to be received within the oblong slots 35 of guide arms 22 with a friction fit. In order to facilitate assembly, the lands 90 can have a length less than the length of slots 35 to permit longitudinal movement or adjustment of the guide arms 22 along lands 90 and relative to housing 27. The housing 27 can be of multi-pad construction to facilitate assembly. If desired, a fluid conduit 91, as shown in FIG. 2, can be positioned on, in or through the surgical saw, the fluid conduit 91 having a first end for being coupled with a source of fluid, such as saline, and a second end for delivering the fluid to the cutting blades for irrigation and/or cooling.

The saw assembly 12 is typically supplied as shown in FIGS. 1–3 with the proximal ends of guide arms 22 disposed in channel 82 of housing 27. Lands 90 are received in slots 35 with the arcuate rearward edges 32 of the guide arms adjacent the circumferential edge segments 75 of the sprocket wheels 72 such that portions of the sprocket wheels are received in the recesses 33 at the proximal ends of the guide arms. As shown in FIG. 3, the sprocket wheels 72 have a diameter that is the same as the lateral dimension of the guide arms 22 between the side edges 31. Each guide arm 22 and corresponding sprocket wheel 72 together define an endless, prescribed track or path extending along forward edge 30 and side edges 31 of the guide arm and along a circumferential portion of the sprocket wheel 72. Each cutting blade 24 is assembled on a guide arm 22 and its associated sprocket wheel 72 with the keels 52 received in spaces 76 of the sprocket wheel 72 and in groove 36 of the guide arm. Accordingly, each cutting blade 24 extends along forward edge 30 and side edges 31 of a guide arm 22 and along a circumferential portion of the corresponding sprocket wheel 72 for movement in a cutting direction along the defined path when the sprocket wheel is rotated. The cutting bands 24 are of a size to fit taut around the guide arms and corresponding sprocket wheels, and, where the lands 90 are shorter in length than the slots 35, the guide arms 22 can be moved longitudinally during assembly to insure that the cutting blades 24 are taut. Where slots 35 are greater in length than lands 90, spacers 92 can be inserted in slots 35 between the lands 90 and the guide arms 22 to maintain the guide arms 22 stationary during use as shown in FIG. 3. The arcuate rearward edges 32 of the guide arms have a radius of curvature corresponding to the radius of curvature of sprocket wheels 72; however, the configuration of rearward edges 32 does not have to correspond to the curvature of the sprocket wheels. When assembled to the drive mechanism, guide arms 22 are laterally spaced from one another such that the cutting teeth 38 intermesh slightly along the inner side edges 31 of the guide arms with a passage or channel 93 defined between the inner side edges 31. The guide arms 22 with the cutting blades 24 guided thereon protrude from the forward end 81 of the housing with the cutting blades 24 being movable through the channel 82 in the cutting direction relative to the stationary guide arms 22.

Figure 9:
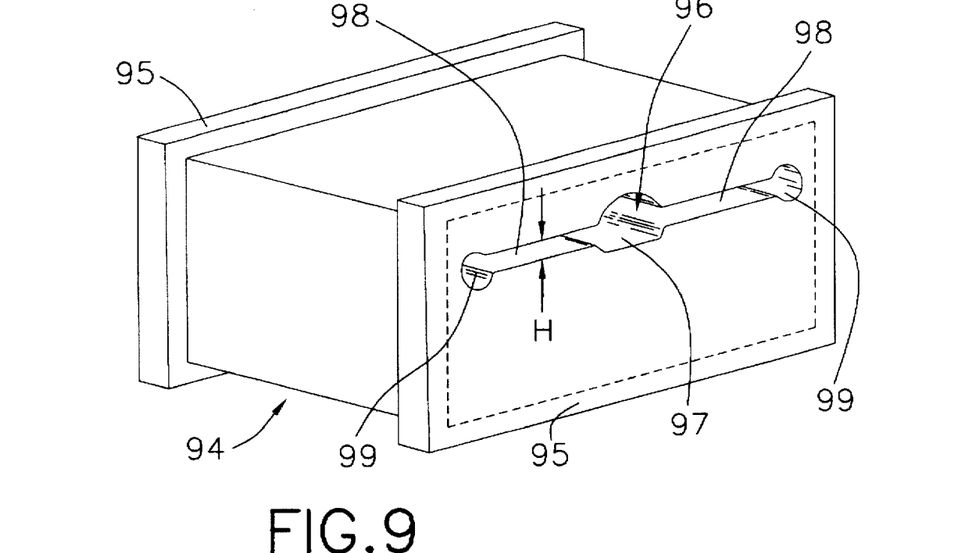
FIG. 9 is a perspective view of a cutting guide for the surgical saw.

FIG. 9 illustrates a cutting guide 94 for use with the surgical saw according to the present invention. Cutting guide 94 includes a rectangular shaped body having flanges 95 at opposite ends thereof and a slot 96 extending entirely through the body for receiving a portion of the saw assembly protruding from housing 27. Slot 96 has an inner or central section 97, intermediate sections 98 flanking inner section 97 and outer sections 99 flanking intermediate sections 98. Inner section 97 has a somewhat rounded configuration in cross-section with a cross-sectional size to receive teeth 38 along the inner sides of guide arms 22. Intermediate sections 98 have a rectangular cross-sectional configuration with a height H to receive thickness T of guide arms 22, the height H being smaller than the kerf K of cutting teeth 38. Outer sections 99 have a rounded configuration in cross-section with a cross-sectional size to receive guard members 83 and teeth 38 along the outer sides of guide arms 22. Cutting guide 94 is preferably made of flexible, pliable or deformable material such as polypropalene allowing the cutting guide to be squeezed to enlarge, open or change the configuration of slot 96 to facilitate sliding of the cutting guide 94 over guide arms 22, cutting bands 24 and guard members 83. The cutting guide 94 can be made in various ways such as injection molding.

In use, the saw assembly 12 is coupled with the handpiece 14 to couple the handpiece drive shaft 20 with shaft 55 of the saw assembly. The cutting guide 94 is squeezed and is slid over the distal end of the saw assembly to position guide arms 22, with cutting bands 24 disposed therearound, and guard members 83 within slot 96. With the cutting guide 94 disposed on the saw assembly, passage 93 and the cutting teeth 38 along the inner sides of guide arms 22 are positioned in slot inner section 97, guide arms 22 are positioned in slot intermediate sections 98, and guard members 63 and the teeth 38 along the outer sides of guide arms 22 are positioned in slot outer sections 99. The guide 94 can be positioned adjacent or in abutment with the forward end of housing 27 as shown in FIG. 9 with the guide arms 22 and guard members 83 protruding from cutting guide 94. The handpiece 14 is held via handgrip 17, and button B is pressed to supply power from power supply P to motor M to rotate drive shaft 20 and bevel gears 54 and 56. Accordingly, gears 64 and 66 will be counter-rotated along with drums 62 and 68 and sprocket wheels 72. Counter-rotation of sprocket wheels 72 causes the cutting bands 24 to be counter-rotated or moved in opposite directions around the guide arms and sprocket wheels, the cutting bands 24 moving through the slot 96 of the guide 94. Accordingly, each cutting band 24 is continuously moved in the cutting or forward direction along the defined path as shown by the arrows in FIG. 3. The distal ends of the guide arms 22 are inserted into anatomical tissue, such as bone, to cut the tissue in the plane of the guide arms, and the saw assembly 12 can be inserted into the bone via a guide block G affixed to the bone as shown in FIG. 10.

Figure 10:
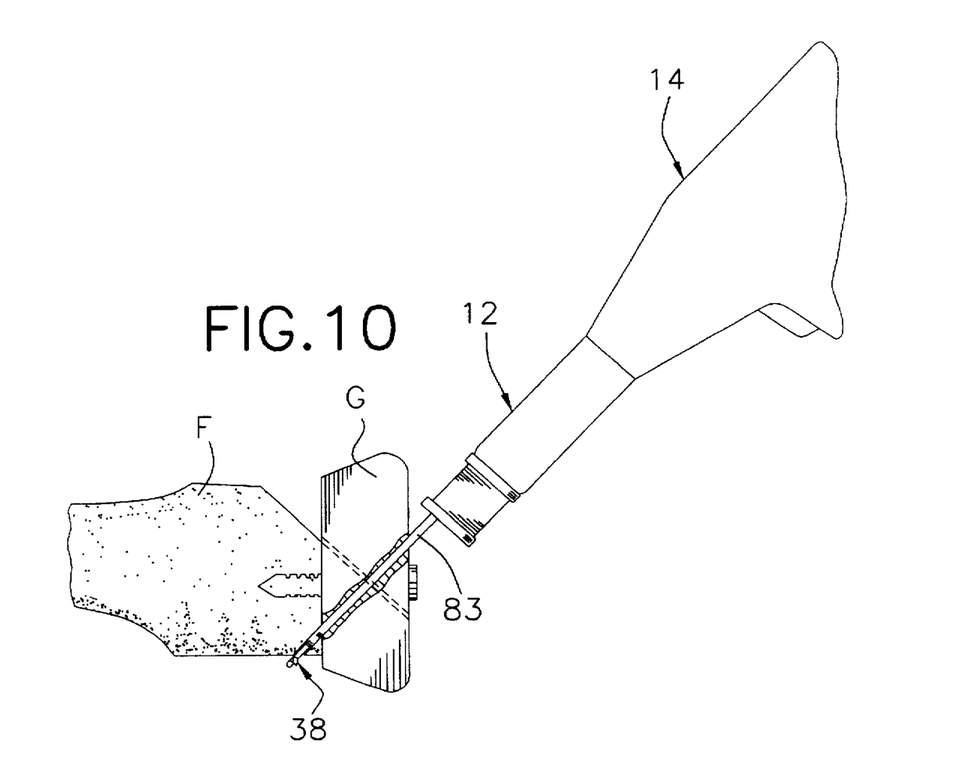
FIG. 10 is a broken side view, partly in section, illustrating use of the surgical saw and cutting guide to resect the femur.

FIG. 10 illustrates the guide arms 22 inserted into the femur F to resect the femur along a plane defining a desired chamfer cut. The guide arms 22 are moved forwardly into and through the bone with a plunge and/or sweeping cutting action to cut the bone along the plane of the guide arms to the desired depth. The guard members 83 follow the guide arms into the cut, and undesired cutting of soft tissue adjacent the bone is prevented since the guard members prevent cutting along most of the outer sides of the guide arms. Debris generated by the cutting action is carried away from the cutting site along passage 93 between the guide arms 22, the debris being carried through the inner section of slot 96. The cutting teeth 38 move past the brush 87 within housing 27 causing debris carried by the cutting teeth to be removed therefrom for collection in sump 89. Once the bone cut is completed to the desired depth, the saw assembly is withdrawn from the bone.

Since the guide arms do not move, friction between the guide arms and the guide block G is minimized such that the temperature of the surgical saw is also minimized. Friction between the guide arms and the bone is also greatly reduced thereby reducing operating temperatures. Accordingly, thermal-necrosis of the bone can be avoided allowing the use of cementless implants. Continuous counter-rotation of the cutting bands, as well as the significantly greater number of cutting teeth for the cutting bands, i.e. typically 9 times more cutting teeth than conventional end cutting oscillating saws, provide enhanced cutting action with less tooth wear. The surgical saw can be operated at lower speeds than conventional end cutting oscillating saws for a reduction in power requirements as well as friction. Cutting debris is effectively removed from the operative or cutting site via the passage between the guide arms in continuous flow cutting. The surgical saw reduces the risk of contamination to operating personnel since splattering of tissue and fluids is greatly reduced due to the stationary guide arms. Since the guide arms do not move, the surgical saw can be more precisely guided during cutting and allows a greater depth of bone cut to be obtained. The two counter-rotating cutting bands nullify side thrusts which are normally produced with end cutting oscillating saws. The surgical saw is self-centering and parallelism of the guide arms is maintained with the use of the cutting guide. The surgical saw is of reduced weight and mass for enhanced stability and deeper bone cuts. The surgical saw can be utilized with conventional guide blocks, and the cutting guide can straddle the conventional guide blocks. The guard members provide for end cutting in a plunge or sweep cutting action while preventing undesired side cutting. The guard members stabilize the saw for a parallel cut and protect against soft tissue damage.

The surgical saw according to the present invention can be utilized with various conventional powered handpieces incorporating various diverse power supplies. The saw assembly can be designed as a removable attachment for the handpieces, or the saw assembly can be designed as part of the handpiece itself. The drive mechanism can be part of the saw assembly, part of the handpiece or an adaptor for being interposed between the saw assembly and the handpiece. Various components of the surgical saw can be designed for disposability after a single use or reusability for multiple uses. The saw assembly can be designed to permit replacement or interchangeability of the guide arms and/or the cutting bands. The saw assembly can include a pair of guide arms with cutting bands thereon as disclosed and illustrated for surgical saw 10, or the saw assembly can include a single guide arm and corresponding cutting band. With the use of holes and/or slots in the guide arms, the weight and mass of the guide arms can be greatly reduced. The guide arms can be longitudinally adjustable relative to the housing to ensure mounting of the cutting bands thereon with a desired tension. The drive mechanism can be designed to provide rotation of the cutting bands at the same speed as the handpiece driveshaft, or the drive mechanism can be designed to reduce or increase the speed of the handpiece driveshaft. Where a fluid conduit is provided, the conduit can be disposed externally of the surgical saw or within the surgical saw, partially or entirely. Various fluids can be supplied to the cutting site, the guide arms or the cutting bands via the conduit for irrigation, cooling and other purposes.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical saw comprising
   a pair of flexible, endless cutting bands having cutting edges for resecting anatomical tissue;
   an elongate guide arm for each cutting band, said guide arms being disposed parallel to and coplanar with one another for guiding said cutting bands for movement in defined paths;
   a housing for mounting said guide arms in parallel, coplanar relationship; and
   a drive system for driving said cutting bands to move around said guide arms, respectively, in said defined paths to resect the anatomical tissue.

2. A surgical saw as recited in claim 1 wherein said guide arms have proximal ends disposed in said housing and distal ends disposed externally of said housing and said drive system drives said cutting bands to counter-rotate around said guide arms.

3. A surgical saw as recited in claim 2 wherein said drive system includes a pair of gears rotatable in opposite directions to move said cutting bands in said defined paths.

4. A surgical saw as recited in claim 3 wherein each of said cutting bands includes a plurality of cutting teeth defining said cutting edges and connected to one another by band segments and a keel for each cutting tooth between said band segments, and wherein each of said gears is rigidly connected to a sprocket wheel including a plurality of spaces along the circumference thereof for receiving said keels, each of said cutting bands being disposed around one of said sprocket wheels and one of said guide arms.

5. A surgical saw as recited in claim 4 and further including a groove in each of said guide arms for receiving said keels of said cutting teeth.

6. A surgical saw as recited in claim 5 wherein said drive system includes a powered surgical handpiece.

7. A surgical saw as recited in claim 6 wherein said guide arms are laterally spaced from one another to define a channel therebetween for removing cutting debris.

8. A surgical saw as recited in claim 7 wherein said guide arms have distal ends and outer sides and further including a pair of guard members extending distally from said housing along said outer sides, said guard members terminating at distal ends disposed proximally of said distal ends of said guide arms.

9. A surgical saw as recited in claim 1 and further including a cutting guide for being secured to the anatomical tissue and having a body with a slot therethrough allowing passage of said guide arms through said slot to access the anatomical tissue, said cutting bands being movable through said slot to cut the anatomical tissue.

10. A surgical saw comprising a flexible, endless cutting band constructed as one piece and including a plurality of spaced cutting teeth for resecting anatomical tissue and connected to one another by band segments;

a stationary guide arm for guiding said cutting band for movement therealong in a cutting direction to resect anatomical tissue;

a drive mechanism for driving said cutting band to move relative to said guide arm in said cutting direction;

a housing for mounting said guide arm and said drive mechanism; and a handpiece for being coupled with said housing to supply power to said drive mechanism.

11. A surgical saw as recited in claim 10 wherein each of said cutting teeth includes a leading surface joined to one of said band segments and defining an acute rake angle therewith, a trailing surface joined to another one of said band segments and meeting said leading surface at an apex and a cutting edge at said apex.

12. A surgical saw as recited in claim 11 wherein said cutting teeth are angled from said band segments in said cutting direction.

13. A surgical saw as recited in claim 12 wherein each of said cutting teeth has a base between two of said band segments and said cutting band further includes a rounded protrusion at said base of each cutting tooth for stabilizing said cutting band.

14. A surgical saw as recited in claim 13 wherein said band segments each have lateral surfaces and said cutting edges protrude laterally beyond said lateral surfaces, said cutting edges of alternate cutting teeth protruding laterally in opposite directions beyond said lateral surfaces.

15. A surgical saw as recited in claim 14 wherein said guide arm has a hole therein for weight reduction.

16. A surgical cutting blade for cutting bone comprising a flexible, endless cutting band including a plurality of cutting teeth spaced from one another by band segments, each of said cutting teeth having a leading surface extending from a band segment at an acute angle and a trailing surface extending from another band segment to meet said leading surface at a cutting edge, said cutting edges of said teeth protruding laterally beyond a lateral plane of said band segments with said cutting edges of adjacent teeth protruding laterally in opposite directions.

17. A surgical cutting blade as recited in claim 16 wherein each of said cutting teeth includes a pair of lateral surfaces transverse to said cutting edge.

18. A surgical cutting blade as recited in claim 17 wherein each of said band segments includes a pair of lateral surfaces and said lateral surfaces of said cutting teeth are angled laterally from said lateral surfaces of said band segments.

19. A surgical cutting blade as recited in claim 18 wherein said lateral surfaces of each of said cutting teeth are parallel to one another.

20. A surgical cutting blade as recited in claim 19 wherein said lateral surfaces of each of said band segments are parallel to one another.

21. A method of resecting bone comprising the steps of providing a surgical saw having a pair of flexible, endless cutting bands for cutting bone, a pair of guide arms coplanar and parallel with one another for guiding the cutting bands, respectively, for movement in a cutting direction along defined paths and having distal ends and proximal ends;

moving the cutting bands relative to and around the guide arms, respectively, in the cutting direction along the defined paths;

inserting the distal ends of the guide arms in the bone to move the cutting bands through the bone in the cutting direction to resect the bone along the plane of the guide arms;

advancing the guide arms forwardly into the bone to resect the bone to a desired depth; and withdrawing the guide arms from the bone to withdraw the cutting bands therefrom.

22. A method of resecting bone as recited in claim 21 wherein said step of moving includes rotating the cutting bands around the guide arms in opposite directions.

23. A method of resecting bone as recited in claim 21 wherein said step of providing includes providing a cutting guide having a slot therethrough and further including, prior to said step of inserting, the step of placing the cutting guide against the bone and wherein said step of inserting includes inserting the guide arms through the slot of the cutting guide to cut the bone.

24. A method of resecting bone as recited in claim 21 and further including the step of supplying fluid to the cutting bands.

25. A method of resecting bone as recited in claim 22 wherein said step of providing includes providing a passage between the guide arms and further including the step of removing cutting debris through the passage.

* * * * *